(12) United States Patent
Relton

(10) Patent No.: US 6,252,055 B1
(45) Date of Patent: Jun. 26, 2001

(54) CONCENTRATED ANTIBODY PREPARATION

(75) Inventor: Julian Marcus Relton, Sevenoaks (GB)

(73) Assignee: Glaxo Wellcome Inc., Triangle Park, NC (US)

( * ) Notice: Subject to any disclaimer, the term of this patent is extended or adjusted under 35 U.S.C. 154(b) by 0 days.

(21) Appl. No.: 09/180,485

(22) PCT Filed: May 22, 1997

(86) PCT No.: PCT/EP97/02595

§ 371 Date: Nov. 12, 1998

§ 102(e) Date: Nov. 12, 1998

(87) PCT Pub. No.: WO97/45140

PCT Pub. Date: Dec. 4, 1997

(30) Foreign Application Priority Data

May 24, 1996 (GB) .................................................. 9610992

(51) Int. Cl.⁷ ........................ C07K 16/00; A61K 39/395; C12N 5/20
(52) U.S. Cl. .................. 530/414; 424/130.1; 424/177.1; 435/326; 530/388.1; 530/387.1; 530/390.5
(58) Field of Search ................................. 435/343.2, 326; 530/388.2, 388.75, 414, 390.5, 388.1, 387.1; 424/133.1, 174.1, 177.1, 130.1

(56) References Cited

U.S. PATENT DOCUMENTS 5,668,003 * 9/1997 Kim et al. .

5,766,947 * 6/1998 Rittershaus et al. .

FOREIGN PATENT DOCUMENTS

| 684 164 | 7/1994 | (CH) . |
| 42 11 169 | 6/1993 | (DE) . |
| 0 064 210 | 11/1982 | (EP) . |
| 0 661 060 | 7/1995 | (EP) . |
| 94 15640 | 7/1994 | (WO) . |

OTHER PUBLICATIONS

Velez et al. Biotech. & Bioeng.; vol. 33; p. 938–940, 1989.*

Database WPI Week 8949 Derwent Publications Ltd., London, GB; AN 89–359879 XP002023849 & JP 01 268 646 A (Meiji Milk Products KK), Oct. 26, 1989 cited in the application see abstract.

Biotechnology and Bioengineering, vol. 33, No. 7, Feb. 20, 1989, New York, NY, USA, pp. 938–940, XP000005263 D. Velez et al.: Use of tangential flow filtration in perfusion propagation of hybridoma cells for production of monoclonal antibodies.: see the whole document.

* cited by examiner

Primary Examiner—David Saunders
Assistant Examiner—Amy DeCloux
(74) Attorney, Agent, or Firm—Nixon & Vanderhye P.C.

(57) ABSTRACT

Concentrated monoclonal antibody preparations for administration to humans are described in which the antibody is present at a concentration of greater than 100 mg/ml and as high as 350 mg/ml.

5 Claims, No Drawings

CONCENTRATED ANTIBODY PREPARATION

This application is a national stage filing under 35 USC 371 from PCT/EP97/02595, filed May 22, 1997.

The present invention relates to a concentrated antibody preparation, pharmaceutical formulations containing such a preparation, its use in human therapy and processes for its preparation.

Most commercially available immunoglobulins produced at high concentration are derived from human serum and produced by the blood products industry. The first purified human immunoglobulin G (IgG) preparation used clinically was immune serum globulin which was prepared in the 1940's (Cohn, E. J. et al 'Preparation and properties of serum and plasma proteins'. J. Am. Chem. Soc. pg68, 459–475 (1946) and Oncley, J. L et al 'The separation of antibodies, isoagglutinins, prothrombin, plasminogen and β-lipoproteins into sub-fractions of human plasma.' J. Am. Chem. Soc. 71, 541–550 (1949)).

The next generation of purified IgG's were developed in the 1960's, and focused on preparations suitable for intravenous administration (Barandun, S.et al 'Intravenous administration of human γ-globulin.' Vox. Sang. 7, 157–174 (1962)).The first of these—IgG intravenous preparation (Gamimune®, Cutter Biological), was formulated as a 5% (50 mg/ml) IgG solution in 0.2 M glycine, 10% maltose, pH 6.8. This solution was stable for at least 2.5 years at 5° C. Key criteria for the acceptance of intravenous IgG (IVIG) products were that the IgG had undergone little fragmentation and that no high molecular weight aggregates were present.

Today, human therapeutic immunoglobulin products are available for either intramuscular (IMIG) or intravenous (IVIG) administration. IMIG are used principally for hepatitis A prophylaxis and sometimes for the treatment of agammaglobulinaemic patients. IVIG are used in the treatment of primary immunodeficiencies and idiopathic thrombocytopenic purpura, as well as for secondary immune deficiencies, various infections, haematological and other autoimmune diseases. In general IMIG products are marketed as 16% (w/v) (160 mg/ml) solutions and IVIG products as 5% (w/v) solutions (50 mg/ml).

Manufacturers experience with IVIG has shown that these preparations are unstable in relatively dilute solutions (<10% (w/v)), and the instability is manifested by the formation of insoluble particles by a process known as 'shedding' when the material is stored at room temperature (Fernandes, P. M. and Lundband, J. L. 'Preparation of a stable intravenous gamma-globulin: process design and scale up.' Vox. Sang. 39, 101–112 (1980)). Commercially available 16.5% γ-globulin is usually stabilised in a buffered glycine-saline solution. The use of maltose at 5–10% as a stabiliser has been shown to be effective in protecting 5% IVIG from particulate formation (Fernandes et al supra).

In addition to shedding, concentrated (16.5%) solutions of IVIG have a tendency to aggregate during long term storage. As much as 10–30% (w/w) of the IVIG solution could be comprised of aggregates (Gronski, P.et al,'On the nature of IgG dimers. I. Dimers in human polyclonal IgG preparations: kinetic studies.' Behring Inst. Mitt. 82, 127–143 (1988)).

The majority of these aggregates are dimers produced by complexes of idiotypic and anti-idiotypic antibodies. Since monoclonal antibodies prepared from tissue culture supernatants do not contain anti-idiotype antibodies, these sort of dimers are absent. However, dimer formation in these preparations can be caused by complexation between partially denatured monomeric antibody molecules. Mechanical stress such as that encountered during tangential flow ultrafiltration used for concentrating antibody preparations can also lead to an increase in aggregation (Wang, Y.-C. J. and Hanson, M. A. 'Parenteral formulations of proteins and peptides: stability and stabilisers.' J. Parenteral Sci. Technol. 42, Suppl. S3–S26 (1988)).

Concentrated (>100 mg/ml) preparations of immunoglobulins are therefore available but to date these are polyclonal antibody preparations derived from the blood processing industry, and are stabilised by the addition of various excipients such as glycine and maltose.

It is therefore surprising that monoclonal antibody preparations have been obtained at a concentration >100 mg/ml in the absence of excipients and without a concomitant increase in aggregates.

The Derwent Abstract of JP01268646A (AN89-359879) reports that the application describes an injection preparation of an $IgG_3$ monoclonal antibody having a concentration of 0.1 μg to 100 mg/ml. Subject matter disclosed in these publications is outside the scope of the instant invention.

The present invention therefore provides a monoclonal antibody preparation for administration to a human characterised in that the antibody in said preparation is at a concentration of 100 mg/ml or greater, preferably greater than 100 mg/ml. Above a concentration of 350 mg/ml the preparation can be very viscous and recovery rates become unacceptably low. The ideal concentration is between 100 and 300 mg/ml.

Preparations according to the invention are substantially free from aggregate. Acceptable levels of aggregated contaminants would be less that 5% ideally less than 2%. Levels as low as 0.2% are achievable, although approximately 1% is more usual. The preparation is also preferably free from excipients traditionally used to stabilise polyclonal formulations, for example glycine and/or maltose.

The present invention therefore provides a monoclonal antibody preparation for administration to a human characterised in that the antibody in said preparation is at a concentration of 100 mg/ml or greater, preferably greater than 100 mg/ml and the preparation is substantially free from aggregate.

Recombinant antibodies by their very nature are produced in a synthetic and unnatural cell culture environment. Expression systems which are used to generate sufficient quantities of the protein for commercialisation are routinely based on myeloma or chinese hamster ovary (CHO) host cells.

In order to culture such cells, complex synthetic media which are devoid of contaminating animal protein have been devised resulting in glycosylation patterns of the protein which would not be expected to arise in nature. It is therefore all the more surprising that a complex glycoprotein produced under such synthetic conditions can be prepared at concentrations several times greater than would occur in normal human serum with all its buffering capabilities.

The present invention therefore provides a monoclonal antibody preparation for administration to a human characterised in that the antibody in said preparation is a recombinant antibody and is at a concentration of 100 mg/ml or greater, preferably greater than 100 mg/ml. The preparation is preferably substantially free from aggregate.

During the production of purified antibodies whether for therapeutic or diagnostic use, it is important that the antibody is sufficiently stable on storage and various chemical entities may have an adverse effect on the stability of the antibody. For example, trace amounts of copper (Cu++) are now known to have a destabilising effect on immunoglobulin molecules on storage (WO93/08837), and that this effect can be eliminated by formulating the immunoglobulin molecule with a suitable chelator of copper ions, for example EDTA or citrate ion.

The present invention is applicable to a preparation of immunoglobulins of all classes, i.e. IgM, IgG, IgA, IgE and IgD, and it also extends to a preparation of Fab fragments and bispecific antibodies. The invention is preferably applied to a preparation of immunoglobulins of the class IgG, which includes the sub-classes $IgG_1$, $IgG_2$, $IgG_3$ and $IgG_4$. The invention is more preferably applied to a preparation of immunoglobulins of the class $IgG_4$ and $IgG_1$, most preferably $IgG_1$.

The invention finds particular application in the preparation of recombinant antibodies, most particularly chimaeric antibodies or humanised (CDR-grafted) antibodies. Particular examples of these include chimaeric or humanised antibodies against CD2, CD3, CD4, CD5, CD7, CD8, CD11a, CD11b, CD18, CD19, CD23, CD25, CD33, CD54, and CDw52 antigen. Further examples include chimaeric or humanised antibodies against various tumour cell markers e.g 40 kd (J.Cell Biol. 125 (2) 437–446 (1994)) or the antigens of infectious agents such as hepatitis B or human cytomegalovirus. Particularly preferred examples include chimaeric or humanised antibodies against CDw52, CD4 and CD23 antigen.

Immunoglobulins intended for therapeutic use will generally be administered to the patient in the form of a pharmaceutical formulation. Such formulations preferably include, in addition to the immunoglobulin, a physiologically acceptable carrier or diluent, possibly in admixture with one or more other agents such as other immunoglobulins or drugs, such as an antibiotic. Suitable carriers include, but are not limited to, physiologic saline, phosphate buffered saline, glucose and buffered saline, citrate buffered saline, citric acid/sodium citrate buffer, maleate buffer, for example malic acid/sodium hydroxide buffer, succinate buffer, for example succinic acid/sodium hydroxide buffer, acetate buffer, for example sodium acetate/acetic acid buffer or phosphate buffer, for example potassium dihydrogen orthophosphate/disodium hydrogen orthophosphate buffer. Optionally the formulation contains Polysorbate for stabilisation of the antibody. Alternatively the immunoglobulin may be lyophilised (freeze dried) and reconstituted for use when needed by the addition of water and/or an aqueous buffered solution as described above.

The preferred pH of the pharmaceutical formulations according to the invention will depend upon the particular route of administration. However, in order to maximise the solubility of the antibody in the concentrated solution, the pH of the solution should be different from the pH of the isoelectric point of the antibody.

Thus, according to a further aspect the invention provides a monoclonal antibody preparation for administration to a human characterised in that the antibody in said preparation is at a concentration of 100 mg/ml or greater and the pH of the preparation is different from the pH of the isoelectric point of the antibody.

Routes of administration are routinely parenteral, including intravenous, intramuscular, and intraperitoneal injection or delivery. However, the preparation is especially useful in the generation of sub-cutaneous formulations which must be low in volume for example approximately 1 ml in volume per dose. To ensure that therapeutic dosage can be achieved in such a formulation, a concentrated preparation will invariably be necessary. Preferred concentrations for sub-cutaneous preparations are for example in the range of 100 mg/ml to 200 mg/ml, for example 150 mg/ml to 200 mg/ml. A sub-cutaneous preparation has the advantage that it can be self-administered thus avoiding the need for hospitalisation for intravenous administration.

Preferably, sub-cutaneous formulations according to the invention are isotonic and will be buffered to a particular pH. The preferred pH range for a sub-cutaneous formulation will in general range from pH 4 to pH 9. The preferred pH and hence buffer will depend on the isoelectric point of the antibody concerned as discussed above. Thus, in the case of sub-cutaneous preparations containing anti-CD4 antibodies the pH will preferably be in the range of pH 4 to pH 5.5, for example pH 5.0 to pH 5.5 e.g. pH 5.5, and in the case of anti-CD23 antibodies in the range of pH 4 to pH 6.5. Thus, preferred buffers for use in sub-cutaneous formulations containing anti-CD4 antibodies are maleate, succinate, acetate or, more preferably phosphate buffers. Buffers are preferably used at a concentration of 50 mM to 100 mM.

Sub-cutaneous formulations according to the invention may also optionally contain sodium chloride to adjust the tonicity of the solution.

Thus, according to a further aspect of the invention provides a monoclonal antibody preparation for sub-cutaneous administration to a human characterised in that the antibody in said preparation is at a concentration of 100 mg/ml or greater and the pH of the preparation is different from the pH of the isoelectric point of the antibody.

In a further aspect of the invention the monoclonal preparation is envisaged for use in human therapy. Various human disorders can be treated such as cancer or infectious diseases for example those mentioned above, and immune disfunction such as T-cell-mediated disorders including severe vasculitis, rheumatoid arthritis, systemic lupis, also autoimmune disorders such as multiple sclerosis, graft vs host disease, psoriarsis, juvenile onset diabetes, Sjogrens' disease, thyroid disease, myasthenia gravis, transplant rejection, inflammatory bowel disease and asthma.

The invention therefore provides the use of a concentrated monoclonal antibody preparation as described herein in the manufacture of medicament for the treatment of any of the aforementioned disorders. Also provided is a method of treating a human being having any such disorder comprising administering to said individual a therapeutically effective amount of a preparation according to the invention.

The dosages of such antibody preparations will vary with the conditions being treated and the recipient of the treatment, but will be in the range 50 to about 2000 mg for an adult patient preferably 100–1000 mg administered daily or weekly for a period between 1 and 30 days and repeated as necessary. The doses may be administered as single or multiple doses.

An antibody preparation may be concentrated by various means such as cross flow (tangential) or stirred ultrafiltration, the preferred route is by tangential flow ultrafiltration. Low recovery rates and precipitate formation can be a problem when concentrating antibody. The present invention solves this particular problem by a method of concentration which involves reducing shear stresses of cross flow ultrafiltration at high circulation rates (500 ml/min). Reducing the recirculation for example to 250 ml/min leads to successful concentration of antibody to >150 mg/ml and to the high recovery of material.

The invention therefore provides a process for the preparation of a concentrated antibody preparation as described herein. The recovery of the antibody in the concentrated preparation is preferably greater than 70% but is routinely greater than 90%.

Concentrated antibody preparations prepared according to the above process may contain additional ingredients such as buffers, salts, Polysorbate and/or EDTA. These additional agents may not be required in the final pharmaceutical formulation in which case they can be removed or exchanged using diafiltration according to conventional methods known in the art. For example, concentrated antibody preparations containing citrate buffer and EDTA can be converted into concentrated antibody preparations containing phosphate or maleate buffer using this method.

The invention also provides a novel concentrated antibody preparation obtainable by such methods.

The following are non-limiting examples of the invention.

EXAMPLE 1
Concentration of Campath 1 H

The Minitan ultrafiltration rig (Minitan XX42 ASY MT Ultrafiltration System, Millipore) was assembled with 2 polysulphone 30K NMWCO filter plates (Minitan PTTK 30K NMWCO,Millipore), and the tubing and plates were sanitised for 30 min with 0.1 M NaOH according to manufacturers instructions (Minitan Ultrafiltration System: Assembly, Operation, Maintenance Instructions, Millipore Corporation, P15076). The sanitant was removed by flushing with 1–2 liters of phosphate buffered saline (PBS), pH 7.2.

Campath-1H (a humanised antibody against the CDw52 antigen: Reichmann et al Nature, 332,323–327 (1988))(2200 ml at 16.4 mg/ml in 50 mM sodium citrate, pH 6.0), was circulated through the retentate side of the membranes at a flux rate of 600 ml/min at a back pressure of 2–2.5 bar. The back pressure was maintained at this value throughout the remainder of the experiment, and the permeate flux rate measured at various time intervals. Samples of antibody were removed from the retentate vessel at various time points and assayed for antibody concentration, turbidity, % aggregate and viscosity.

Because the filtration rate was so slow in this experiment it was neccessary to carry out the concentration over 3 days. The system was flushed out with PBS, and the concentrate stored overnight at 4° C. After day 2, 0.01% (w/v) Thiomersal was added to the concentrate before overnight storage to prevent microbial contamination. At the end of the concentration, the system was flushed out with 500 ml of PBS, then a further 500 ml flush of PBS was recirculated around the retentate side of the membranes for 30 min. The concentration of antibody in these flushes was determined by measuring the absorbance at 280 nm.

The total time taken to concentrate Campath-1H from 16.4 mg/ml to 257 mg/ml using only 2 plates in the Minitan was 17.25 hours. Table 1(a) shows the change in concentration of Campath-1H over this time. The concentration TABLE 1(a)

| Time (h) | 0 | 5 | 6.5 | 9.5 | 11.5 | 12.5 | 14.5 | 16 | 17 | 17.25 |
|---|---|---|---|---|---|---|---|---|---|---|
| Conc (mg/ml) | 16 | 34 | 41 | 79 | 106 | 136 | 190 | 230 | 301 | 257 | increased in an exponential manner to a peak of 300 mg/ml after 17 hours. The final concentration was slightly lower than this peak value; the discrepancy probably due to the difficulty in obtaining a representative sample from a very viscous liquid. Table 1(b) shows that the concentration of Campath-1H was accompanied by a reciprocal decrease in the flow rate of the permeate. This TABLE 1(b)

| Conc (mg/ml) | 16 | 34 | 41 | 79 | 106 | 136 | 189 | 301 | 257 |
|---|---|---|---|---|---|---|---|---|---|
| Flow (ml/min) | 4 | 3 | 2.5 | 1.5 | 1.25 | 0.9 | 0.5 | | |
| Viscosity (cPs) | 1 | 1 | 1 | 1 | 1 | 1 | 0.96 | 4.85 | 8.1 |

Table also shows there was a dramatic increase in the viscocity of the remaining concentrate above a concentration of 189 mg/ml.

Table 1(c) shows that the recovery was high up to a concentration of 190 mg/ml, but started to decline markedly above this concentration as the viscosity increase led to material sticking to glassware and tubing and being lost during flushing prior to overnight storage. The final recovery of 257 mg/ml material TABLE 1(c)

| Conc (mg/ml) | 16 | 41 | 106 | 190 | 257 |
|---|---|---|---|---|---|
| Rec (%) | 100 | 97 | 97 | 85 | 63 |

(excuding material removed during sampling and lost in washes) was 63.4%. A further 14.6% was recovered in the first PBS wash of the system and 0.5% in the second, recirculated PBS wash. In total, therefore, 78.5% of the initial material was recovered at the end of the experiment (excuding material removed during sampling and lost in washes), leaving a loss of 21.5% mainly due to viscous material sticking to glassware and plastics.

Turbidity of the Campath-1H solution during concentration was calculated. The absorbance of suitably diluted 1.0 ml aliquots of antibody samples at 650 nm was used as a measure of turbidity. Table 1 (d) shows that there was no increase.

TABLE 1(d)

| Conc (mg/ml) | 16 | 41 | 79 | 106 | 136 | 190 | 301 | 257 |
|---|---|---|---|---|---|---|---|---|
| Rec (%) | 0.96 | 1.16 | 1.1 | 0.91 | 1 | 1.01 | 1.11 | 1.01 |
| Aggregate (%) | 0.002 | 0.015 | 0.023 | 0.032 | 0.042 | 0.032 | 0.035 | |

Samples for aggregate determination were diluted to a protein concentration of 1 mg/ml using PBS and 50 μl or 100 μl aliquots injected onto a TSK-GEL G3000SW$_{XL}$ size exclusion HPLC column. The column was developed with 0.05% NaN$_3$ and 0.1 M Na$_2$SO$_4$ in 0.1 M phosphate buffer, pH 6.7 at a flow rate of 1.0 ml/min. The amount of aggregate was determined by integrating the peaks of absorbance at 280 nm and were found to remain around 1% throughout.

EXAMPLE 2

Concentration of Anti-CD4 Antibody—Method A

The Minitan ultrafiltration rig was assembled and sanitised as in Example 1 except that 8 polysulphone 30K NMWCO filter plates were used instead of 2, and the whole rig was placed in a sterile hood. Anti-CD4 antibody (2142 ml at 13.9 mg/ml in 50 mM sodium citrate, pH 6.0) was circulated through the retentate side of the membranes at a flux rate of 190 ml/min at a back pressure of 2–2.5 bar. The back pressure was maintained at this value throughout the remainder of the experiment, and the permeate flux rate measured at various time intervals. Samples of antibody were removed from the retentate vessel at various time points and assayed for antibody concentration, CD4 binding, turbidity, % aggregate and viscosity.

At the end of the experiment the retentate was pumped out of the Minitan rig and the retentate side of the membranes was flushed with 500 ml of 50 mM sodium citrate, 0.05 mM EDTA, pH 6.0 and 50 ml fractions of the flush were collected. Finally, the system was flushed by recirculating 500 ml of 50 mM sodium citrate, 0.05 mM EDTA, pH 6.0 around the retentate side of the membrane for 30 min. The antibody concentration of the flush fractions was determined by measuring their absorbance at 280 nm.

The results are shown in Tables 2(a)–(d). The increase in the number of plates used for the concentration led to a decrease in the time taken to achieve a concentration of 250 μg/ml–250 mg/ml to 6 h compared to the 17.25 h for the Campath-1H concentration (see Table 2(a)). Table 2(a) also shows that the viscosity of the Anti-CD4 antibody did not measurably increase until a concentration of 113 mg/ml was achieved. Above this concentration the viscocity increased dramatically.

TABLE 2(a)

| Time (h) | 0 | 2 | 3.5 | 5 | 6 |
|---|---|---|---|---|---|
| Conc mg/ml | 13.9 | 47.2 | 83 | 112.8 | 252 |
| Viscosity cPs | 1 | 1 | 1 | 1 | 9.7 |

At concentrations above 83 mg/ml there was a noticable opalescence in the concentrated material, and this caused a precipitate to form as the concentration increased above this value. This led to the decrease in flux rates of the permeate shown in Table 2(b) and also to the rise in turbidity shown in Table 2(c). The level of aggregate remained very low at all concentrations, being less than 0.2% throughout (see Table 2(c)). Table 2(b) shows that recoveries were high until the viscocity increased and the precipitate occured, where they fell dramatically to a final recovery in the retentate after removal from the rig of 50%.

TABLE 2(b)

| Conc mg/ml | 13.9 | 47.2 | 83 | 112.8 | 252 |
|---|---|---|---|---|---|
| Rec (%) | 100.0 | 100.0 | 100.0 | 113.0 | 51.4 |
| Flow (ml/min) | 13.5 | 3.2 | 2.0 | 2.5 | |

TABLE 2(c)

| Conc mg/ml | 13.9 | 47.2 | 83 | 112.8 | 252 |
|---|---|---|---|---|---|
| Turb A650 nm | 0.011 | 0.012 | 0.030 | 0.185 | |
| Agg (%) | 0.140 | 0.150 | 0.150 | 0.160 | 0.170 |

This poor recovery was due to the high viscosity of the concentrated Anti-CD4 antibody making it stick to the tubing and membranes of the ultrafiltration system. All the Anti-CD4 antibody lost in this way could be subsequently recovered by flushing out the system with buffer. Table 2(d) shows the recovery of Anti-CD4 antibody in successive 50 ml wash fractions during the flushing out of the Minitan rig at the end of the experiment. The first fraction contains 11.7 g of Anti-CD4 antibody at a concentration of 235 mg/ml, so this could be pooled with the 12.6 g of concentrate initially recovered from the rig at 252 mg/ml without significantly diluting the overall concentration. The remaining wash fractions contained a total of 5.1 g of Anti-CD4 antibody, but this was at a concentration of less than 57 mg/ml, so could not be pooled with the concentrated material. The overall recovery in the concentrate and the first wash fraction was 90%. It was noticed that after storage of the final concentrated Anti-CD4 antibody overnight at 4° C. led to some of the precipitate redissolving.

TABLE 2(d)

| ml | 50 | 100 | 150 | 200 | 250 | 300 | 350 | 400 | 450 | 500 |
|---|---|---|---|---|---|---|---|---|---|---|
| mg | 11727 | 2828 | 866 | 379 | 245 | 202 | 175 | 151 | 132 | 125 |

An experiment was therefore set up to determine the concentration at which the precipitated Anti-CD4 antibody was completely resolubilised. A 10 ml aliquot of Anti-CD4 antibody at 250 mg/ml was progressively diluted by the addition of 50 mM sodium citrate, 0.05 mM EDTA, pH 6.0. The absorbance of suitably diluted 1.0 ml aliquots of antibody samples at 650 nm was used as a measure of turbidity. The results are shown in Table 3.

TABLE 3

| Conc mg/ml | 237.7 | 149.5 | 110.4 | 88.6 | 76.3 | 60.3 |
|---|---|---|---|---|---|---|
| Turb (A650 nm) | 1.17 | 0.096 | 0.082 | 0.074 | 0.03 | 0.027 |

The precipitate redissolved, but the turbidity and opalescence did not disappear completely until a Anti-CD4 antibody concentration of about 80 mg/ml was reached. It was above this concentration that the opalescence was first observed during the concentration, so the precipitate seems to be reversible and to be concentration dependant.

EXAMPLE 3

Concentration of Anti-CD4 Antibody-Method B

Buffer Adjustment of Anti-CD4 Antibody

The Anti-CD4 antibody (1460 ml; 24 g) was prepared in 50 mM sodium citrate, 0.05 mM EDTA, pH 6.0. This buffer was made up to ~100 mM sodium citrate, 0.05 mM EDTA, pH 6.0 by adding solid citric acid to the antibody preparation and adjusting the pH to 6.0 with NaOH. The resulting preparation was sterile filtered through a 0.22 μm filter and stored as 2 aliquots of ~12 g.

Anti-CD4 Antibody Concentration in Filtron Ultrasette

The Filtron Mini-Ultrasette and Watson-Marlow pump were placed in a cold room. The Mini-Ultrasette (30 K cut-off cross-flow ultrafilter Filtron) was flushed with water then sanitised for 30 min with 0.1 M NaOH according to manufacturers instructions. (Mini Ultrasette Tangential Flow Device Operating Instructions & Mini Ultrasette Care and Use Manual., Filtron Technology Corporation). The sanitant was removed by flushing with sterile water followed by 1–2 liters of sterile PBS, pH 7.2 until the pH of the effluent was 7.2. Anti-CD4 was circulated through the retentate side of the membranes at a flux rate of 250 ml/min throughout.

After concentating the Anti-CD4 antibody to ~150 mg/ml the retentate was pumped out of the Mini-Ultrasette and the retentate side of the membranes was flushed with 3×20 ml of 50 mM sodium citrate, 0.05 mM EDTA, pH 6.0 and each 20 ml fraction of the flush was collected. The antibody concentration of the flush fractions was determined by measuring their absorbance at 280 nm as described in Example 1.

The results suggested that reducing the retentate flux rate may provide a method for concentrating anti-CD4 to ~150 mg/ml by cross flow ultrafiltration and avoiding any precipitation. This was tested using the Filtron Mini-Ultrasette and a retentate circulation rate of 250 ml/min.

A suitable isotonic buffer for this work was 100 mM sodium citrate, 0.05 mM EDTA, pH 6.0. Therefore the remaining 1460 ml of anti-CD4 in 50 mM sodium citrate, 0.05 mM EDTA, pH 6.0 was reformulated by adding 16.8 g of citric acid and the pH of the final solution was adjusted with NaOH. This material was sterile filtered and divided into 2 equal aliquots which were then separately concentrated in the Filtron ultrafiltration device using a recirculation rate of 250 ml/min. The results are shown in Table 4.

Table 4: Concentration of Anti-CD4 to Greater than 100 mg/ml in a Cross Flow Ultrafiltration Cell at 250 ml/min Recirculation Rate

TABLE 4

Concentration of Anti-CD4 to greater than 100 mg/ml in a Cross Flow Ultrafiltration Cell at 250 ml/min Recirculation Rate

| Parameter | Before Concentration | Concentration 1 | Concentration 2 |
|---|---|---|---|
| Maximum Concentration achieved (mg/ml) | — | 169 | 156 |
| Concentration of final product (mg/ml) | 14.4 | 106.4 | 100.5 |
| Recovery after concentration (%) | — | 90 | 95 |
| Time taken for concentration (h) | — | 11 | 9 |
| Aggregate (%) * | 4.14 | 3.95 | 3.97 |
| Turbidity (A650 nm) | 0.003 | 0.018 | 0.037 |
| Osmolality (mOs/kg) | 281 | 288 | 306 |
| CD4 Binding (mg/ml) | 20 | 98.8 | 68.3 |

*Aggregate analysis by Size Exclusion HPLC

Samples for aggregate determination were diluted to a protein concentration of 1 mg/ml using PBS and 50 μl or 100 μl aliquots injected onto a TSK-GEL G3000SW$_{XL}$ size exclusion HPLC column. The column was developed with 0.05% $NaN_3$ and 0.1 M $Na_2SO_4$ in 0.1 M phosphate buffer, pH 6.7 at a flow rate of 1.0 ml/min. The amount of aggregate was determined by integrating the peaks of absorbance at 280 nm.

Both concentrations achieved a maximum concentration of >150 mg/ml in the ultrafiltration apparatus with no deleterious affects on antibody solubility. The concentrations took 9–11 h. The final concentrations of ~100 mg/ml were a result of dilution with the washes required to maximise recovery from the ultrafiltration apparatus. Overall recoveries were 90–95%, and no visible precipitate or increase in levels of aggregate were observed. The slight rise in turbidity after concentration as measured by the absorbance at 650 nm caused a slight opacity of the final concentrate, but this was removed on formulation with Polysorbate 80 and sterile filtration and was not considered significant.

The CD4 binding activity for concentration 1 was almost 100 mg/ml as expected, but a much lower value was obtained for concentration 2. The final osmolality of the pooled material from concentrations 1 and 2 was approximately 297 mOs/kg, and the pool was a clear, bright solution that could easily pass through a sterile 0.2 μm filter.

Anti-CD4 Antibody Concentration in Stirred Cell

A 330 ml aliquot of Anti-CD4 antibody (as above) was concentrated at 5° C. in an Amicon stirred ultrafiltration cell (fitted with YM30 membrane Amicon) to a final concentration of 170 mg/ml by applying a pressure of 1.5 bar using nitrogen gas. The Anti-CD4 antibody in the ultrafiltration cell was sampled at intervals and the concentration determined by measuring the absorbance at 280 nm and the turbidity by measuring the absorbance at 650 nm. At the end of the experiment, the concentrated material was removed from the ultrafiltration cell and sterile filtered through a 0.22 μm filter.

To overcome the high shear forces generated on the Filtron cross-flow ultrafiltration apparatus, concentration was carried out in a stirred ultrafiltration cell using 50 mM sodium citrate, 0.05 mM EDTA, pH 6.0 as the buffer. Table 5 shows the results from this experiment.

TABLE 5

Concentration by Ultrafiltration of Anti-CD4 in an Amicon Stirred Cell

| Time (h) | Volume of Retentate (ml) | Approximate Concentration of Retentate (mg/ml) | Ultrafiltration Flux Rate (ml/h) |
|---|---|---|---|
| 0 | 330 | 16.7 | — |
| 6 | 150 | 37 | 30 |
| 9 | 100 | 55 | 17 |
| 11 | 75 | 73 | 12 |
| 14 | 46 | 120 | 10 |
| 38 | 40 | 134 | 0.25 |
| 54 | 27 | 171* | 0.81 |

* Actual concentration determined by measuring absorbance at 280 nm.

In total the concentration took about 2.5 days, and the flux rates declined rapidly as the viscocity of the concentrated antibody increased. A final concentration of 171 mg/ml was successfully achieved with no evidence of precipitation. This material was removed from the ultrafiltration cell and the membrane was washed with sufficient 50 mM sodium citrate, 0.05 mM EDTA, pH 6.0 to give a final concentration of 100 mg/ml when pooled with the concentrate.

This material easily passed through a 0.2 μm sterile filter. The actual measured concentration of this pooled material was 94.3 mg/ml in a volume of 46 ml. This corresponded to a recovery across the ultrafiltration step of 79%.

This experiment therefore provided evidence that 50 mM sodium citrate, 0.05 mM EDTA, pH 6.0 was a suitable buffer for concentration of anti-CD4 to at least 171 mg/ml, and that it was probably the high shear forces that were causing the precipitation in the original cross-flow ultrafiltration experiments in both the Minitan and the Filtron Mini-Ultrasette noted above.

EXAMPLE 4
Sub-cutaneous Formulation for Anti-CD4 and Anti-CD23 Antibodies

| Sub-cutaneous formulations for anti-CD4 and anti-CD23 antibodies | |
|---|---|
| a) Anti-CD4 or Anti-CD23 antibody | 0.15 g |
| Potassium dihydrogen orthophosphate, $KH_2PO_4$ (anhydrous) | 0.0656 g |
| Disodium hydrogen orthophosphate, $Na_2HPO_4 \cdot 12H_2O$ | 0.0673 g |
| NaCl | 0.6263 g |
| Polysorbate 80 (% of total formulation weight) | 0.01 |
| Water | to 100 g |
| b) Anti-CD4 or Anti-CD23 antibody | 0.15 g |
| Na acetate | 3.674 g |
| Glacial acetic acid, 10% solution | 0.315 g |
| NaCl | 0.630 g |
| Polysorbate 80 (% of total formulation weight) | 0.01 |
| Water | to 100 g |
| c) Anti-CD4 or Anti-CD23 antibody | 0.15 g |
| Maleic acid | 0.227 g |
| 0.5M NaOH | 6.09 g |
| NaCl | 0.777 g |
| Polysorbate 80 (% of total formulation weight) | 0.01 |
| Water | to 100 g |
| d) Anti-CD4 or Anti-CD23 antibody | 0.15 g |
| Succinic acid | 0.203 g |
| 0.5M NaOH | 6.54 g |
| NaCl | 0.779 g |
| Polysorbate 80 (% of total formulation weight) | 0.01 |
| Water | to 100 g |

NB. Each of formulations a), b), c) or d) may optionally contain 0.05 mM EDTA.

What is claimed is:

1. A method of producing a concentrated antibody preparation comprising the steps of:

(a) providing an antibody preparation;

(b) filtering said antibody preparation through a retentate side of a filtering membrane using ultrafiltration to produce a filtrate; and (c) circulating said filtrate back to said retentate side of the filtering membrane at a circulation rate of less than 500 ml/min thereby reducing sheer stress on said filtrate.

2. The method according to claim 1 wherein greater than 70% of said antibody preparation is recovered into said concentrated antibody preparation.

3. The method according to claim 2 wherein greater than 90% of said antibody preparation is recovered into said concentrated antibody preparation.

4. A method of producing a concentrated antibody preparation comprising the steps of:

(a) providing an antibody preparation;

(b) filtering said antibody preparation through a retentate side of a filtering membrane using ultrafiltration to produce a filtrate; and (c) circulating said filtrate back to said retentate side of the filtering membrane at a circulation rate of 250 ml/min thereby reducing sheer stress on said filtrate.

5. A method of producing a concentrated antibody preparation comprising the steps of:

(a) providing an antibody preparation;

(b) filtering said antibody preparation through a retentate side of a filtering membrane using ultrafiltration to produce a filtrate; and (c) circulating said filtrate back to said retentate side of the filtering membrane at a circulation rate of 190 ml/min thereby reducing sheer stress on said filtrate.

* * * * *